(12) United States Patent
Hsiao

(10) Patent No.: US 8,938,159 B2
(45) Date of Patent: Jan. 20, 2015

(54) AROMA-DIFFUSING APPARATUS USING A DISPOSABLE AROMA CAPSULE

(71) Applicant: Ming Jen Hsiao, Road Town (VG)

(72) Inventor: Ming Jen Hsiao, Road Town (VG)

(73) Assignee: Serene House International Enterprise Ltd. (VG)

( * ) Notice: Subject to any disclaimer, the term of this patent is extended or adjusted under 35 U.S.C. 154(b) by 177 days.

(21) Appl. No.: 13/670,430

(22) Filed: Nov. 6, 2012

(65) Prior Publication Data

US 2014/0126891 A1    May 8, 2014

(51) Int. Cl.
*F24F 3/14* (2006.01)
*F24F 6/00* (2006.01)

(52) U.S. Cl.
USPC .......................... 392/392; 392/386; 392/394

(58) Field of Classification Search
None
See application file for complete search history.

(56) References Cited

U.S. PATENT DOCUMENTS

| | | | | |
|---|---|---|---|---|
| 949,606 A * | 2/1910 | Tetherow | ...................... | 219/429 |
| 1,431,719 A * | 10/1922 | Brown | .......................... | 392/403 |
| 1,547,160 A * | 7/1925 | Bailey | ........................... | 219/473 |
| 2,043,647 A * | 6/1936 | Berven | .......................... | 261/136 |
| 2,742,342 A * | 4/1956 | Dew et al. | ....................... | 422/37 |
| 2,881,303 A * | 4/1959 | Resk | .............................. | 392/403 |
| 3,959,642 A * | 5/1976 | Turro | .............................. | 362/92 |
| 4,544,592 A * | 10/1985 | Spector | .......................... | 428/68 |
| 4,647,433 A * | 3/1987 | Spector | ........................ | 422/125 |
| 4,781,895 A * | 11/1988 | Spector | ........................ | 422/125 |
| 5,647,052 A * | 7/1997 | Patel et al. | .................... | 392/390 |
| 5,651,942 A * | 7/1997 | Christensen | .................. | 422/125 |
| 6,031,967 A * | 2/2000 | Flashinski et al. | ............ | 392/390 |
| 6,663,838 B1 * | 12/2003 | Soller et al. | ................... | 422/125 |
| 7,046,919 B2 * | 5/2006 | Shimizu et al. | ................ | 392/390 |
| 7,670,566 B2 * | 3/2010 | Adair et al. | ................... | 422/125 |
| 8,047,837 B2 * | 11/2011 | Furner et al. | .................. | 431/291 |
| 8,147,097 B1 | 4/2012 | Hsiao | | |
| 8,201,957 B2 | 6/2012 | Hsiao | | |
| 8,265,466 B2 * | 9/2012 | Jorgensen | ..................... | 392/393 |
| 8,281,514 B2 * | 10/2012 | Fleming | .......................... | 43/129 |
| 8,716,632 B1 * | 5/2014 | Pesu et al. | ..................... | 219/438 |
| 2005/0016985 A1 * | 1/2005 | Haas et al. | ..................... | 219/438 |
| 2005/0274818 A1 * | 12/2005 | Ghazarian | ....................... | 239/34 |
| 2007/0014549 A1 * | 1/2007 | Demarest et al. | ............. | 392/393 |
| 2007/0047931 A1 * | 3/2007 | Niemeyer | ..................... | 392/390 |
| 2008/0013932 A1 * | 1/2008 | He et al. | ........................ | 392/390 |
| 2011/0128747 A1 | 6/2011 | Hsiao | | |

* cited by examiner

*Primary Examiner* — Thor Campbell
(74) *Attorney, Agent, or Firm* — Chun-Ming Shih

(57) ABSTRACT

An aroma-diffusing apparatus includes a housing defining a top opening, a lamp socket mounted in the housing and holding a lamp bulb, an aroma capsule including a disposable heat-transfer container detachably mounted in the top opening of the housing, a breathing film bonded to the disposable heat-transfer container to hold an aromatic substance held in the disposable heat-transfer container and a sealing film bonded to the heat-transfer container to seal the aromatic substance in the heat-transfer container, and a cable bracket affixed to the lamp socket for keeping the cable from becoming tangled.

9 Claims, 7 Drawing Sheets

AROMA-DIFFUSING APPARATUS USING A DISPOSABLE AROMA CAPSULE

CROSS-REFERENCES TO RELATED APPLICATION

Two pending new application Ser. Nos. 13/543,490 and 13/549,493 filed on Jul. 15, 2012 are hereby incorporated by reference.

FIELD OF THE INVENTION

The present invention relates to scent releasing devices and more specifically, to an aroma-diffusing apparatus that uses a disposable aroma capsule.

DESCRIPTION OF THE RELATED ART

Aroma-diffusing night lamp systems that combine a night lamp unit and an aroma diffuser unit for diffusing a good smell are known. U.S. Pat. No. 8,147,097B1 discloses a similar design. However, during application, the user needs to prepare a particular storage device for holding an aromatic wax or essential oil, and then to carefully pick up the aromatic wax or essential oil from the storage device and to put the aromatic wax or essential oil in an accommodation chamber of a ceramic or glass container above a lampshade of the aroma-diffusing night lamp system for heating by the radiating heat energy of a lamp bulb in the lampshade. During delivery of the aromatic wax or essential oil from the ceramic or glass container, the lamp bulb may be contaminated by the aromatic wax or essential oil accidentally. Further, when the aromatic wax or essential oil is used up, the user needs to clean the accommodation chamber of the ceramic or glass container, avoiding mixing of different aromatic substances or smells. Further, the ceramic or glass container is fragile, and can be broken easily during cleaning.

Further, an aroma-diffusing night lamp system may be equipped with a cable bracket or like member to avoid tangled electrical wires. Similar designs are seen in U.S. patent application Ser. Nos. 12/614,189 and 12/626,979. According to conventional cable bracket designs, electrical wires of lamp socket are curved and extended through a plurality of notches and holes at the cable bracket, and then extended out of the cable bracket for connection to a power source. When extending through the notches and holes of the cable bracket, the electrical wires are curved in a large angle, imparting stress to the molecular chains of the outer insulation of the electrical wires. Further, under the effect of waste heat from the lamp bulb, the mechanical strength of the insulative plastic material of the electrical wires will be lowered. After a long use, the curved area of the outer insulation of the electrical wires can be broken easily, losing its protective function.

Therefore, it is desirable to provide an aroma-diffusing apparatus that eliminates the drawbacks of the aforesaid prior art designs.

SUMMARY OF THE INVENTION

The present invention has been accomplished under the circumstances in view. It is therefore the main object of the present invention to provide an aroma-diffusing apparatus, which utilizes the radiating heat of a lamp bulb to heat a disposable aroma capsule to give off fragrance, and allows replacement of the disposable aroma capsule when it is used up. It is another object of the present invention to provide an aroma-diffusing apparatus, which holds electrical wires in a smoothly curved manner against stretching, avoiding electrical wire damage.

To achieve these and other objects of the present invention, an aroma-diffusing apparatus comprises a housing defining a top opening, a lamp socket mounted inside the housing, a lamp bulb installed in the lamp socket, and an aroma capsule detachably accommodated in the top opening of the housing and heatable by radiating heat from the lamp bulb to give off fragrance. The aroma capsule comprises a heat-transfer container accommodated in the top opening of the housing and defining a top opening, and an aromatic substance held in said disposable heat-transfer container.

Further, the aroma-diffusing apparatus comprises a breathing film bonded to the disposable heat-transfer container to keep the aromatic substance in the disposable heat-transfer container, and a sealing film bonded to the disposable heat-transfer container over the breathing film.

Further, the disposable heat-transfer container is selected from the material group of metal, hard plastics, fibers and compound materials.

Further, the lamp socket has electrical wires electrically connected to respective electrodes therein for connection to power source. Further, a high tensile strength cable bracket is affixed to the electrical socket for securing the electrical wires. The high tensile strength cable bracket is a plate member comprising a mounting lug fixedly connected to the lamp socket, a planar panel, a sloping panel obliquely connected between the mounting lug and the planar panel, a first cable-retaining notch and a second cable-retaining notch respectively and symmetrically located on two opposite lateral sides of the sloping panel, and a third cable-retaining notch and a fourth cable-retaining notch respectively and symmetrically located on two opposite lateral sides of the planar panel.

DETAILED DESCRIPTION OF THE PREFERRED EMBODIMENT

Figure 1:
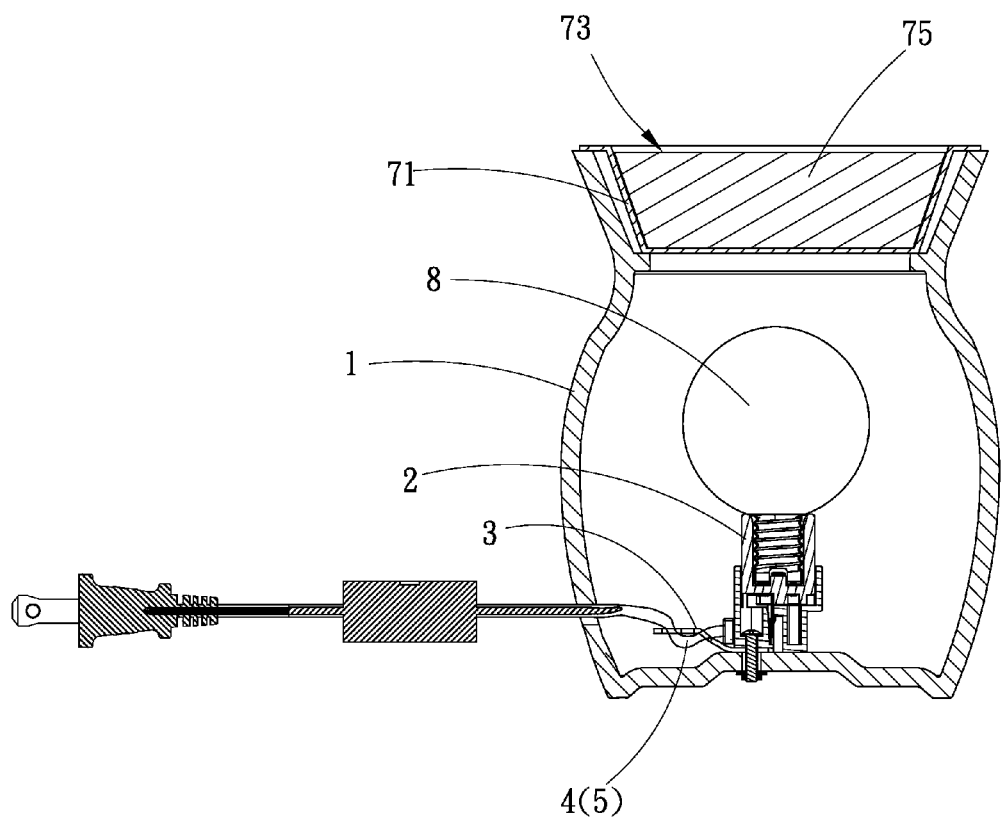
FIG. 1 is a sectional view of an aroma-diffusing apparatus in accordance with the present invention.
Figure 2:
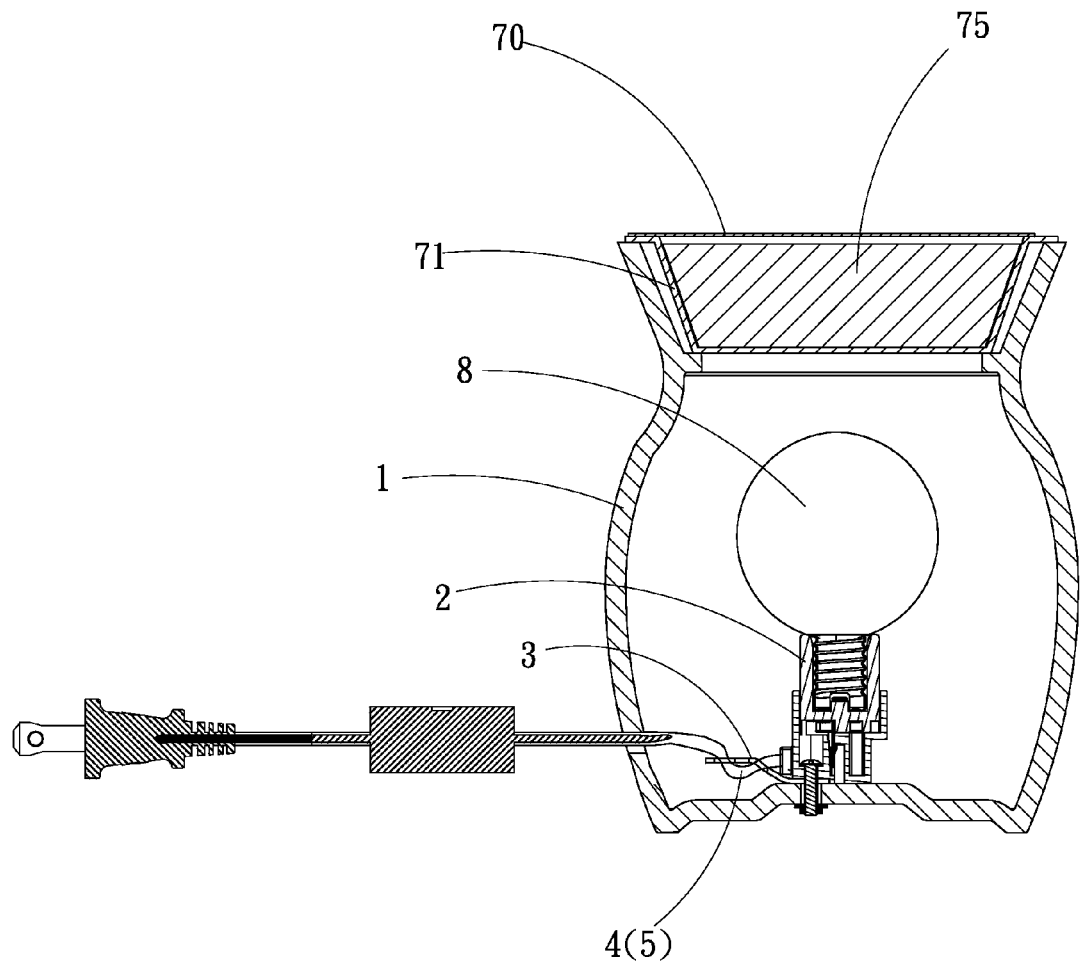
FIG. 2 corresponds to FIG. 1, illustrating a breathing film bonded to the top opening of the disposable heat-transfer container of the aroma capsule.
Figure 3:
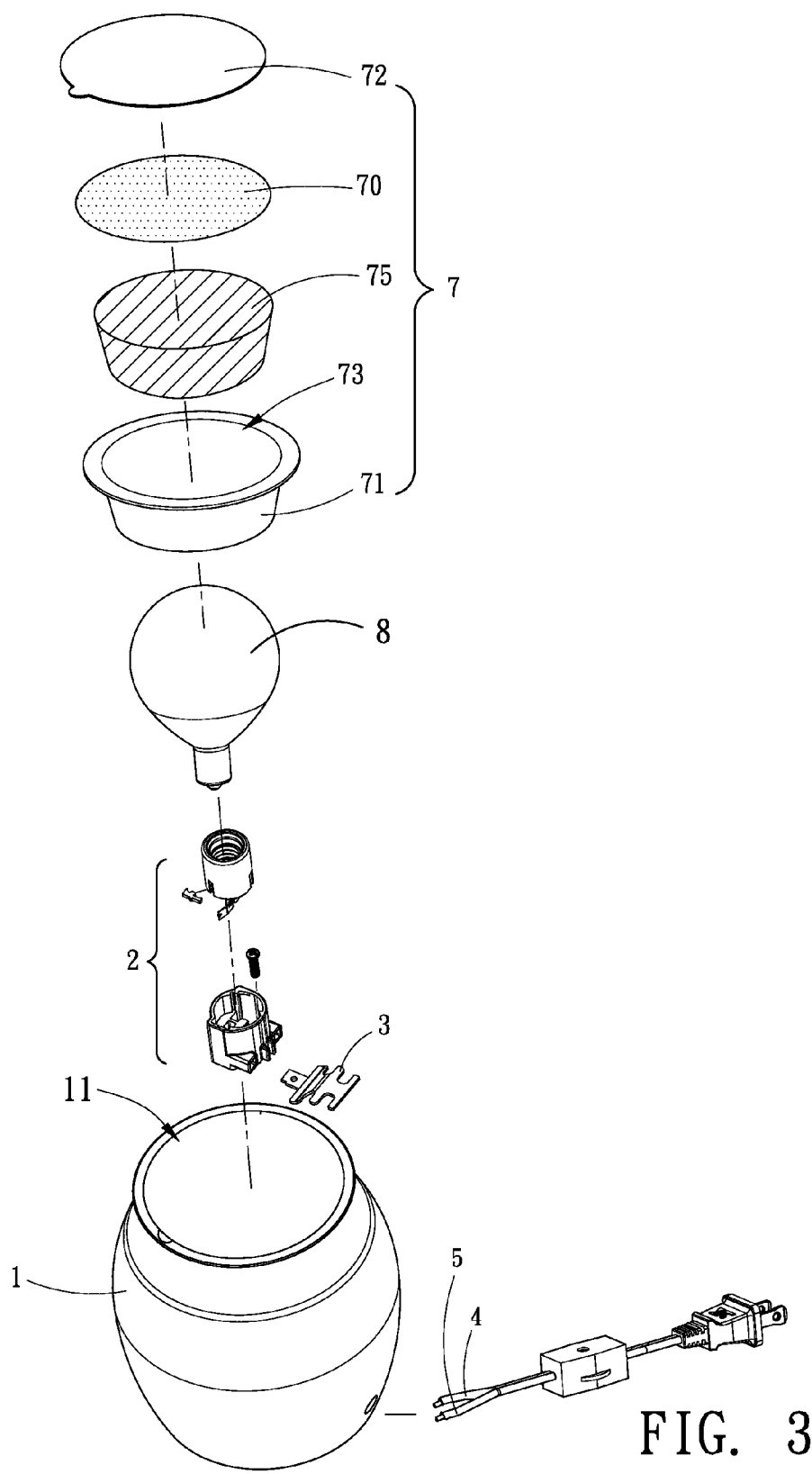
FIG. 3 is an exploded view of the aroma-diffusing apparatus in accordance with the present invention.

Referring to FIGS. 1 and 2, an aroma-diffusing apparatus in accordance with the present invention is shown. The aroma-diffusing apparatus 1 comprises a housing 1 defining a top opening 11 at the top side thereof, a lamp socket 2 mounted inside the housing 1, a bulb 8 installed in the lamp socket 2, and an aroma capsule 7, which comprises a disposable heat-transfer container 71 detachably mounted in the top opening 11 of the housing 1 and defining a top opening 73, an aromatic substance 75 put in the disposable heat-transfer container 71, a breathing film 70 sealed to the top opening 73 over the aromatic substance 75, and a sealing film 72 bonded to the disposable heat-transfer container 71 to seal the aromatic substance 75 in the disposable heat-transfer container 71 to protect the aromatic substance 75 against contamination during delivery and to maintain the quality of the aromatic substance 75.

Further, the aromatic substance 75 can be solid aromatic wax, essential oil, or perfume.

Further, commercial aroma diffusers are commonly capable of diffusing an aromatic smell when heated to the temperature of 35~75° C. In this embodiment, the aromatic substance 75 is aromatic wax. The lamp bulb 8 can heat the aroma capsule 7 to the temperature of 35~75° C., causing the aroma capsule 7 to diffuse a good smell into the outside open air. Under this temperature range, the disposable heat-transfer container 71 will not melt or deform, and can efficiently transfer heat energy produced by the lamp bulb 8 to the aromatic substance 75. The disposable heat-transfer container 71 can be a thin metal film container, a hard plastic container, or a fiber bowl made of a plant fiber such as corn fiber, glass fiber or carbon fiber, or a container of a composite material.

Preferably, the disposable heat-transfer container 71 is made of aluminum film, having the characteristics of lightweight, thin wall thickness and good heat conductivity. Thus, the disposable heat-transfer container 71 can transfer heat energy produced by the lamp bulb 8 to the aromatic substance 75 rapidly, causing the aromatic substance 75 to diffuse a good smell. Further, the disposable heat-transfer container 71 is tough and not easily breakable, eliminating the fragile drawback of ceramic or glass containers that are commonly used in conventional aroma diffusers for holding an essential oil. Further, the sealing film 72 seals the solid aromatic substance 75 in the disposable heat-transfer container 71, maintaining the quality of the aromatic substance 75. Further, the aromatic substance 75 is sealed in the disposable heat-transfer container 71 but not carried in an ordinary container. When using the aromatic substance 75, the user simply needs to remove the sealing film 72 from the disposable heat-transfer container 71 without touching the aromatic substance 75. Further, after the aromatic substance 75 is used up, the user can remove the disposable heat-transfer container 71 from the top opening 11 of the housing 1, and then put a new aroma capsule 7 in the top opening 11 of the housing 1 to replace the used aroma capsule without the necessity of cleaning the used aroma capsule. Further, because the disposable heat-transfer container 71 is made of aluminum foil, it is not breakable. Thus, the user needs not to worry about breaking down the disposable heat-transfer container 71. Further, the user needs not to prepare an extra container for holding the solid aromatic substance 75.

Further, the breathing film 70 is selected from the material group of fabric, fiber cloth, porous plastic membrane and porous metal foil, and adapted to guide diffusing aromatic smell upwardly through open spaces therein toward the outside open air. An user can remove the sealing film 72 from the disposable heat-transfer container 71 conveniently, and then put the disposable heat-transfer container 71 in the top opening 11 of the housing 1, enabling the aromatic substance 75 of the aroma capsule 7 to be heated by the lamp bulb 8 to release a pleasant smell. If the aroma-diffusing apparatus falls to the floor accidentally, the breathing film 70 still can retain the molten aromatic substance, preventing the molten aromatic substance from flowing to the lamp bulb 8 and the lamp socket 2 or to wet the internal circuit of the lamp socket 2, avoiding contamination and ensuring a high level of safety.

Figure 4:
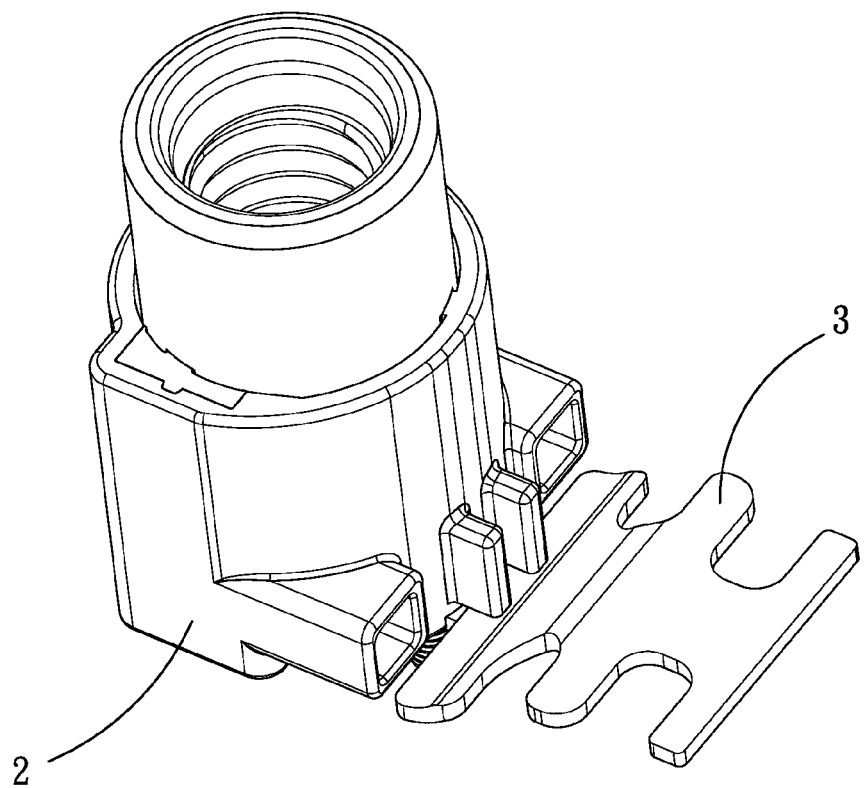
FIG. 4 is an elevational view of a part of the present invention, illustrating a cable bracket affixed to the lamp socket.
Figure 5:
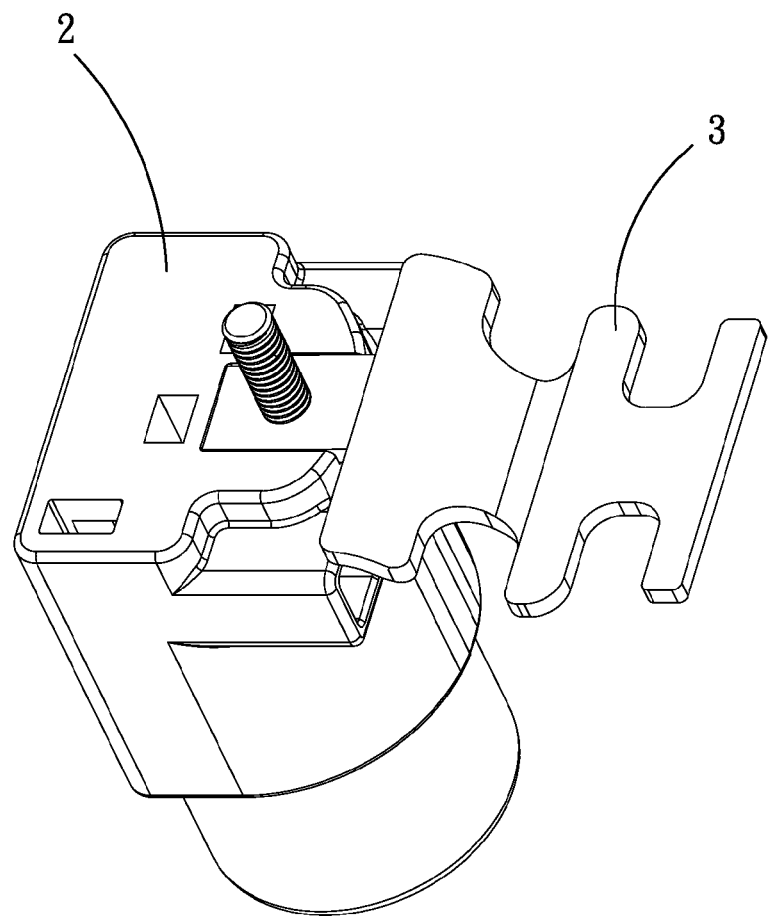
FIG. 5 corresponds to FIG. 4 when viewed from another angle.
Figure 6:
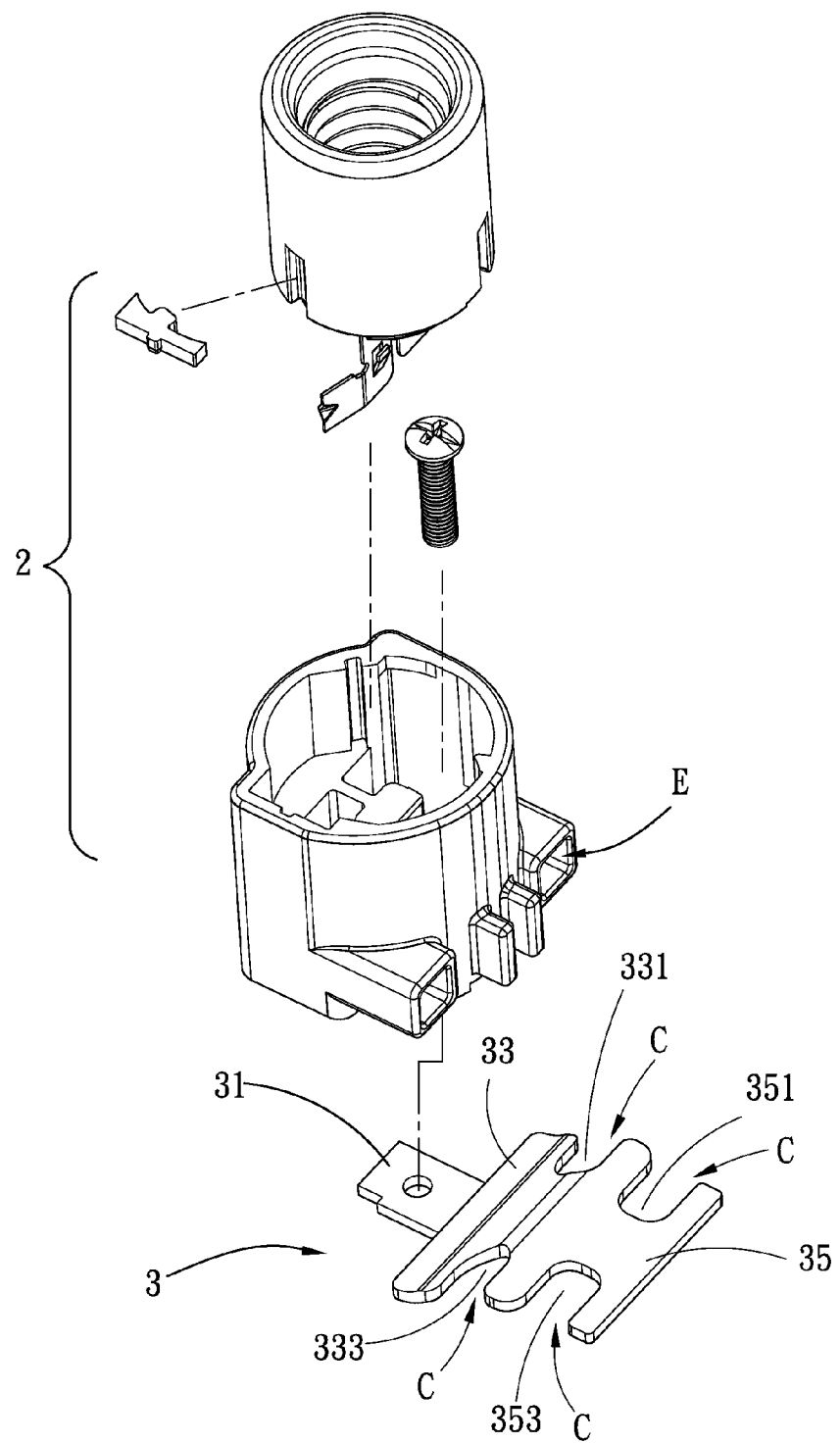
FIG. 6 is an exploded view of the lamp socket and cable bracket assembly shown in FIG. 4.

Referring to FIGS. 4-6 and FIG. 3 again, the aroma-diffusing apparatus further comprises a high tensile strength cable bracket 3. The high tensile strength cable bracket 3 comprises a mounting lug 31 fixedly connected to the lamp socket 2, a planar panel 35, a sloping panel 33 obliquely connected between the mounting lug 31 and the planar panel 35, a first cable-retaining notch 331 and a second cable-retaining notch 333 respectively and symmetrically located on two opposite lateral sides of the sloping panel 33, and a third cable-retaining notch 351 and a fourth cable-retaining notch 353 respectively and symmetrically located on two opposite lateral sides of the planar panel 35.

Each of the cable-retaining notches 331;333;531;533 defines a mouth C. The mouth C has a width relatively shorter than the internal width of the respective cable-retaining notch 331;333;531;533, facilitating quick positioning of electrical wires in the cable-retaining notches 331;333;531;533. Further, through holes can be formed in the sloping panel 33 and the planar panel 35 instead of the cable-retaining notches 331;333;531;533 for securing electrical wires.

Figure 7:
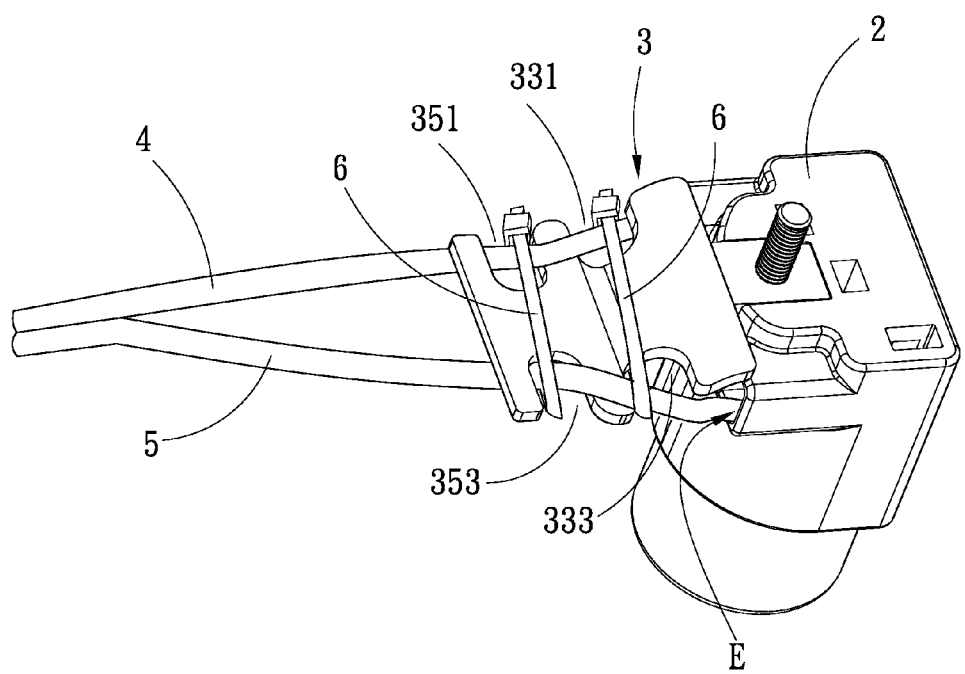
FIG. 7 is an applied view of a part of the present invention, illustrating a first electrical wire and a second electrical wire arranged on the cable bracket and electrically connected to the electrodes of the lamp socket.

Referring to FIG. 7, the lamp socket 2 has a first electrical wire 4 and a second electrical wire 5 electrically connected internal electrodes E thereof. Further, the first electrical wire 4 is inserted from the bottom side of the sloping panel 33 through the first cable-retaining notch 331 toward the top side of the planar panel 35 and then extended downwardly through the third cable-retaining notch 351 to the bottom side of the planar panel 35 and then turned forwardly out of the cable bracket 3 to the power source. The second electrical wire 5 is inserted from the bottom side of the sloping panel 33 through the second cable-retaining notch 333 toward the top side of the planar panel 35 and then extended downwardly through the fourth cable-retaining notch 353 to the bottom side of the planar panel 35 and then turned forwardly out of the high tensile strength cable bracket 3 to the power source.

Thus, the first electrical cable 4 and the second electrical cable 5 are respectively secured to the first and third cable-retaining notches 331;351 of the high tensile strength cable bracket 3 and the second and fourth cable-retaining notches 333;353 of the high tensile strength cable bracket 3, avoiding curving in a large angle. When the electrical wires 4;5 are stretched by an external force, the high tensile strength cable bracket 3 transfer the stretching force to the lamp socket 2, avoiding disconnection of the electrical wires 4;5 from the electrodes E of the lamp socket 2.

Referring to FIGS. 4 and 7 again, the electrodes E are arranged in one side of the lamp socket 2. Preferably, the electrodes E are arranged in the lamp socket 2 in a parallel manner so that the respective ends of the first and second electrical wires 4;5 can be conveniently and straightly connected to the electrodes E in a parallel manner without bending.

Referring to FIG. 7 again, a binding strap 6 is fastened to the high tensile strength cable bracket 3 to hold down the first electrical cable 4 in the first cable-retaining notch 331 of the high tensile strength cable bracket 3 and the second electrical cable 5 in the third cable-retaining notch 333.

Further, another binding strap 6 can be fastened to the high tensile strength cable bracket 3 to hold down the first electrical cable 4 in the second cable-retaining notch 351 of the high tensile strength cable bracket 3 and the second electrical cable 5 in the fourth cable-retaining notch 353.

Further, the high tensile strength cable bracket 3 is prepared by a thermal conductive plate member. When viewed from one side, the high tensile strength cable bracket 3 shows a substantially Z-shaped configuration for supporting the first electrical wire 4 and the second electrical wire 5 in a smoothly curved manner, avoiding internal conductor damage.

Although particular embodiment of the invention have been described in detail for purposes of illustration, various modifications and enhancements may be made without departing from the spirit and scope of the invention. Accordingly, the invention is not to be limited except as by the appended claims.

What the invention claimed is:

1. An aroma-diffusing apparatus, comprising:
a housing defining a top opening at a top side thereof;
a lamp socket mounted inside said housing;
a lamp bulb installed in said lamp socket;
an aroma capsule detachably accommodated in said top opening of said housing and heatable by radiating heat from said lamp bulb to give off fragrance, said aroma capsule comprising a heat-transfer container accommodated in said top opening of said housing, said disposable heat-transfer container defining a top opening, and an aromatic substance held in said disposable heat-transfer container; and
a high tensile strength cable bracket for securing electrical wires, and a first electrical wire and a second electrical wire respectively electrically connected to said lamp socket for connection to an external power source, said high tensile strength cable bracket comprising a mounting lug fixedly connected to said lamp socket, a planar panel, a sloping panel obliquely connected between said mounting lug and said planar panel, a first cable-retaining notch and a second cable-retaining notch respectively and symmetrically located on two opposite lateral sides of said sloping panel, and a third cable-retaining notch and a fourth cable-retaining notch respectively and symmetrically located on two opposite lateral sides of said planar panel, said first electrical wire being inserted from a bottom side of said sloping panel through said first cable-retaining notch toward a top side of said planar panel and then extended downwardly through said third cable-retaining notch to a bottom side of said planar panel and then turned forwardly out of said cable bracket to a power source, said second electrical wire being inserted from the bottom side of said sloping panel through said second cable-retaining notch toward the top side of said planar panel and then extended downwardly through said fourth cable-retaining notch to the bottom side of said planar panel and then turned forwardly out of said high tensile strength cable bracket to said power source.

2. The aroma-diffusing apparatus as claimed in claim 1, said aroma capsule further comprises a breathing film bonded to said disposable heat-transfer container to keep said aromatic substance in said disposable heat-transfer container, said breathing film having open spaces defined therein.

3. The aroma-diffusing apparatus as claimed in claim 2, said aroma capsule further comprises a sealing film bonded to said disposable heat-transfer container over said breathing film.

4. The aroma-diffusing apparatus as claimed in claim 1, said aromatic substance is a block of aromatic wax.

5. The aroma-diffusing apparatus as claimed in claim 2, said breathing film is selected from the material group of fabric, fiber cloth, porous plastic membrane and porous metal foil.

6. The aroma-diffusing apparatus as claimed in claim 1, said disposable heat-transfer container is selected from the material group of metal, hard plastics, fibers and compound materials.

7. The aroma-diffusing apparatus as claimed in claim 1, said disposable heat-transfer container is made in the form of an aluminum foil bowl.

8. The lamp socket and cable bracket assembly as claimed in claim 1, wherein said first cable-retaining notch, said second cable-retaining notch, said third cable-retaining notch and said fourth cable-retaining notch respectively define a mouth, said mouth having a width relatively shorter than the internal width of the respective cable-retaining notch.

9. The lamp socket and cable bracket assembly as claimed in claim 1, further comprising at least one binding strap fastened to said high tensile strength cable bracket to hold down said first electrical cable in said first cable-retaining notch and said second cable-retaining notch and said second electrical cable in said third cable-retaining notch and said fourth cable-retaining notch.

\* \* \* \* \*